United States Patent [19]

Warriner

[11] Patent Number: Plant 6,515

[45] Date of Patent: Jan. 3, 1989

[54] ROSE PLANT JACARE

[75] Inventor: William A. Warriner, Tustin, Calif.

[73] Assignee: Jackson & Perkins Company, Medford, Oreg.

[21] Appl. No.: 27,816

[22] Filed: Mar. 19, 1987

[51] Int. Cl.[4] ..... A01H 5/00

[52] U.S. Cl. ..... Plt./23

[58] Field of Search ..... Plt./23

*Primary Examiner*—James R. Feyrer

*Attorney, Agent, or Firm*—Majestic, Gallagher, Parsons & Siebert

[57] ABSTRACT

A rose variety of the floribunda class is provided having numerous clusters of white flowers contrasted by dark green, glossy foliage and bright orange hip production late in the Fall. The rose plant had a vigorous upright, yet compact growth habit, is resistant to powdery mildew, and the open flowers display attractive, large yellow anthers.

1 Drawing Sheet

SUMMARY OF THE INVENTION

The present invention relates to a new and distinct variety of rose plant of the floribunda class, which was originated by me by crossing the variety Sun Flare, U.S. Plant Pat. No. 5,001, with an unnamed seedling.

The primary objective of this breeding was to produce a new rose variety of the floribunda class exhibiting continuous bloom, strong growth and wide adaptability. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Continuous production of bright white flowers borne in clusters;
2. Contrasting dark green glossy foliage;
3. Bright orange hips;
4. Large anthers attractively displayed in open flowers;
5. Resistance to powdery mildew;
6. Upright, compact growth habit.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "JACARE". Color terminology is in accordance with The Royal Horticultural Society Colour Chart except where an ordinary dictionary significance for the color is apparent.

Observations of the buds and flowers were made from specimens grown in a garden at Irvine, Calif. in October.

Flower

The blooming habit is recurrent and continuous. The bud size is one and one-half inches when the petals start to unfurl. The bud form is long, pointed ovoid. The bud color when sepals first divide is near White 155D; when half blown, the upper side of petals is near White 155D and the lower side of petals is near White 155D. The sepals have a color near Green 138B with occasional reddish streaks. The surface texture is smooth but with occasional reddish glands. There are three appendaged sepals normally to heavily appendaged, and two unappendaged sepals with hairy edge. The receptacle color is near Green 138B with reddish cast of a funnel shape, large size and smooth surface. The peduncle is of short length, and glandular surface. Peduncle color is bronzy and the penduncle is stiff.

Bloom

Bloom size is medium, with an average open size of three to four inches, borne in clusters. The clusters are rounded to flat. The stems are strong and short. The form when first open is high center. This form then flattens and the outer petals curl back. Under normal conditions there are fifteen to twenty petals. The upper side of petals is White 155D, as is the reverse side of the petals. The base of petals has a yellowish spot at the point of attachment to the peduncle with the major color being near White 155D. There are no variegations. The general tonality at the end of the first day shows no change in color. At the end of the third day, there remains no discoloration.

The fragrance is slight. The petal texture is thick, of a deltoid shape and flat with the tips being slightly recurved.

The arrangement is imbricated with no petaloids in the center. The blooms drop off cleanly, and last on the plant for a fair period and as a cut flower for a short time.

Reproductive Parts

The anthers are large and many, of yellow color and arranged regularly around the styles. The filaments are yellow, the pollen is gold yellow, the styles are reddish, and the stigmas are greenish white.

Plant

A very vigorous growth of bush form.

Foliage

Large size, abundant in quantity. The new foliage is reddish, and the old foliage is dark glossy green near Green 139A. Normal mid-stem leaves have five leaflets.

The leaflets are of an oval pointed shape, are leathery and glossy, and have a serrated edge. The serration is single and small in size. Petiole rachis is green and petiole underside is smooth with prickles. Stipules are medium and bearded. The foliage is resistant to mildew under normal growing conditions at Irvine, Calif.

Wood

New wood is light green, with a smooth bark. Old wood is green with a smooth bark.

Prickles

There are an ordinary number of prickles on main canes from the base and on laterals from the main canes. The form is medium and straight. Color when young is green.

Small Prickles

There are no small prickles on the main stalks or on the laterals.

Additional Distinguishing Traits

This novel rose plant sets numerous hips up to one inch diameter. As the hips ripen, they turn orange and then red. They are thick fleshed, juicy, contain little astringency and are somewhat sweet when eaten. The seeds are plump, cream colored and number from five to thirty per hip.

Parentage

The seed parent was Sun Flare, U.S. Plant Pat. No. 5,001. The pollen parent was an unnamed seedling.

Classification

Botanical is rosa hybrid. Commercial is floribunda.

I claim:

1. A new and distinct variety of rose plant and parts thereof of the floribunda class substantially as herein shown and described, characterized particularly as to novelty by the numerous clusters of white flowers contrasted by dark green glossy foliage, vigorous upright yet compact growth habit, bright orange hip production late in the Fall, large yellow anthers attractively displayed in open flowers and resistance to powdery mildew.

* * * * *

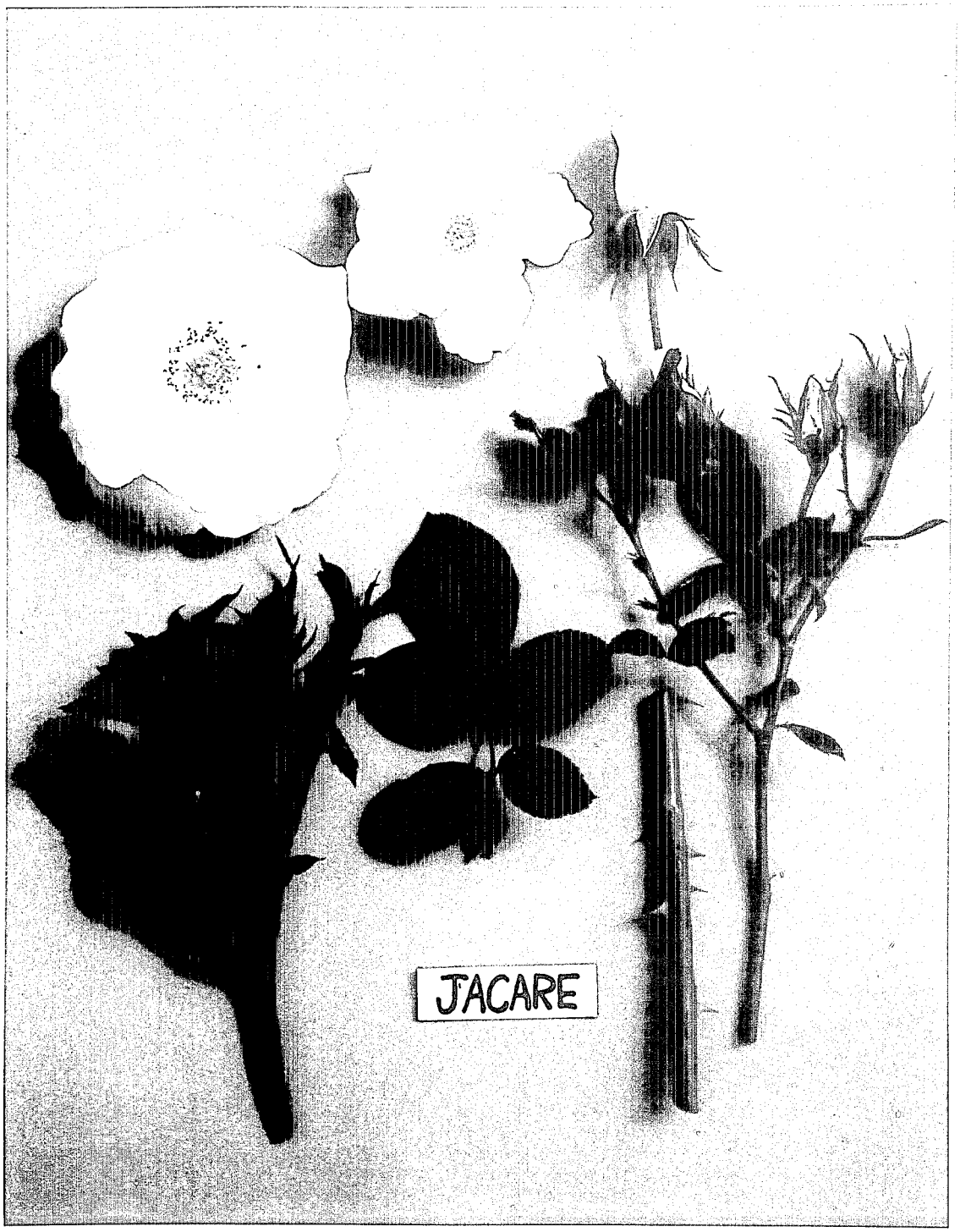
JACARE